(12) United States Patent
Kurzen

(10) Patent No.: US 8,680,149 B2
(45) Date of Patent: Mar. 25, 2014

(54) 1-AMINO-ALKYLCYCLOHEXANE DERIVATIVES FOR THE TREATMENT OF MAST CELL MEDIATED DISEASES

(71) Applicant: Merz Pharma GmbH & Co. KGaA, Frankfurt am Main (DE)

(72) Inventor: Hjalmar Kurzen, Freising (DE)

(73) Assignee: Merz Pharma GmbH & Co. KGaA, Frankfurt am Main (DE)

( * ) Notice: Subject to any disclaimer, the term of this patent is extended or adjusted under 35 U.S.C. 154(b) by 0 days.

(21) Appl. No.: 13/766,145

(22) Filed: Feb. 13, 2013

(65) Prior Publication Data

US 2013/0158124 A1   Jun. 20, 2013

Related U.S. Application Data

(63) Continuation of application No. 12/998,962, filed as application No. PCT/EP2009/009151 on Dec. 18, 2009, now Pat. No. 8,399,519.

(60) Provisional application No. 61/203,194, filed on Dec. 19, 2008.

(30) Foreign Application Priority Data

Dec. 19, 2008   (EP) .................................... 08022151

(51) Int. Cl.
  *A61K 31/13*   (2006.01)

(52) U.S. Cl.
  USPC ......................................... 514/579; 514/659

(58) Field of Classification Search
  USPC ................................................ 514/579, 659
  See application file for complete search history.

(56) References Cited

U.S. PATENT DOCUMENTS

| | | | |
|---|---|---|---|
| 6,057,364 A | 5/2000 | Jasys et al. | |
| 6,221,887 B1 | 4/2001 | Ashgar et al. | |
| 6,616,933 B1 | 9/2003 | Breton et al. | |
| 7,851,501 B2 | 12/2010 | Aydt et al. | |
| 2002/0058010 A1 | 5/2002 | Picard-Lesboueyries et al. | |
| 2004/0102525 A1 | 5/2004 | Kozachuk | |
| 2005/0137122 A1 | 6/2005 | Sharif | |
| 2005/0196418 A1 | 9/2005 | Yu et al. | |
| 2007/0082956 A1* | 4/2007 | Magerl et al. ................. | 514/579 |
| 2007/0141148 A1* | 6/2007 | Hauptmeier et al. ......... | 424/468 |
| 2010/0197792 A1 | 8/2010 | Boderke et al. | |

FOREIGN PATENT DOCUMENTS

| | | |
|---|---|---|
| AU | 2004251636 | 1/2005 |
| EP | 0904777 | 3/1999 |
| EP | 1184031 | 10/2007 |
| EP | 1952797 | 8/2008 |
| WO | WO9532945 | 12/1995 |
| WO | WO9804537 | 5/1998 |
| WO | WO01/88253 | 12/2001 |
| WO | WO2004043899 | 5/2004 |
| WO | WO2005009421 | 2/2005 |
| WO | WO2005044228 | 5/2005 |
| WO | WO2007062815 | 6/2007 |
| WO | WO2007/082206 | 7/2007 |
| WO | WO2007/103687 | 9/2007 |
| WO | WO2007117544 A2 * | 10/2007 |
| WO | WO2007148113 | 12/2007 |

OTHER PUBLICATIONS

Graves et al. Inflammation in amyotrophic lateral sclerosis spinal cord and brain is mediated by activiated macrophages, mast cells and T cells. ALS and other motor neuron disorder 2004 5, pp. 213-219.*
Paul, et al., Journal of Pharmacology and Experimental Therapeutics, 2002, 302, 50-57.
Platt-Mills, Am. J. Respir. Crit. Care Med., 2001. 164, S1-S5.
International Search Report for PCT/EP2009/009151 dated Mar. 19, 2010.
Rammes, G. et al: "Neramexane Merz Pharmaceuticals/Forest Laboratories" IDrugs, Current Drugs LTD, GB, vol. 9, No. 2, Jan. 1, 2006, pp. 128-135, XP007903367 ISSN: 1369-7056 abstract.
Finch, et al., Pain, 2009.
Fuziwara, et al., J. Invest. Dermatol., 2003, 120, 1023-1029.
Interational Search Report for PCT/EP2009/009153 dated Mar. 19, 2010.
Kurzen, et al., Exp. Dermatol., 2004, 13 (Suppl. 4), 27-30.
Kurzen, et al., J. Invest Dermatol., 2004, 123, 937-949.
Plazas, et al., Eur. J. Pharmacol, 2007, 566, 11-19.
Schwarz, et al., Journal of Immunology, 2004, 172, 1036-1043.
Metcalfe, et al., Physiological Reviews, 1997, 77, 1033-1079.

* cited by examiner

*Primary Examiner* — Jennifer M Kim
(74) *Attorney, Agent, or Firm* — Hueschen and Sage

(57) ABSTRACT

The present invention relates to the treatment of an individual afflicted with mast cell mediated diseases comprising administering to the individual an effective amount of a 1-amino-alkylcyclohexane derivative.

11 Claims, 1 Drawing Sheet

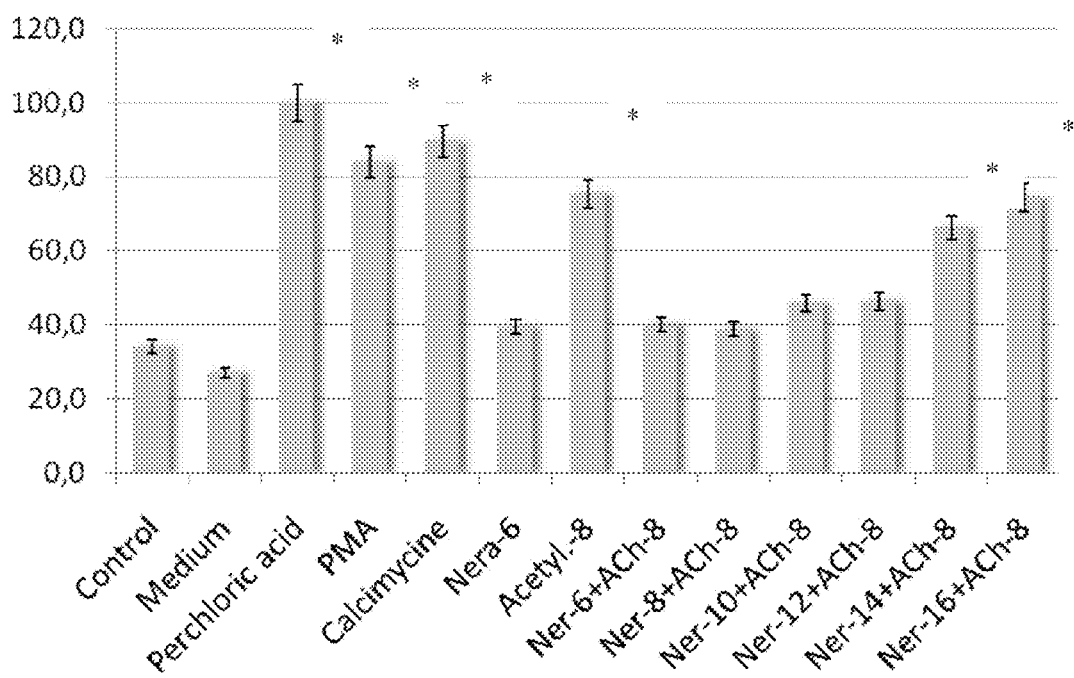
**Effect of Neramexane on mast cell degranulation *in vitro***
Histamine concentration in the culture supernatant is plotted as percent of total histamine concentration defined as 100%, obtained after lysis of the mast cells by perchloric acid.

1-AMINO-ALKYLCYCLOHEXANE DERIVATIVES FOR THE TREATMENT OF MAST CELL MEDIATED DISEASES

FIELD OF THE INVENTION

The present invention relates to the treatment of an individual afflicted with mast cell mediated diseases, comprising administering to the individual an effective amount of a 1-amino-alkylcyclohexane derivative.

BACKGROUND OF THE INVENTION

This invention relates to methods of treating patients afflicted with mast cell mediated diseases, including urticaria, atopic dermatitis, psoriasis, pruritus, asthma, rhinitis, mastocytosis, conjunctivitis and keratoconjunctivitis.

Mast cells (MC) and blood basophils are crucial components of the acquired and innate human immune system. The different subtypes are found in almost all tissues, most abundantly in the skin and the respiratory and gastrointestinal tract. Mast cells are the primary effector cells in immunoglobulin E (IgE) mediated inflammatory reactions and are involved in maintenance of skin and mucosal homeostasis as well as in neurohumoral interactions associated with various inflammatory processes, such as allergic inflammation. Mast cells are involved in certain inflammatory dermatologic diseases, such as urticaria, cutaneous mastocytosis, atopic dermatitis and psoriasis and in the polyetiological pruritus. Mast cells are also involved in extracutaneous diseases such as rhinitis, systemic mastocytosis, allergic and non-allergic asthma bronchiale, conjunctivitis and keratoconjunctivitis. A key event in mast cell triggered inflammatory processes is mast cell degranulation, in which an extensive mixture of different cytokines and neurotransmitters (such as serotonin and/or histamine) is delivered to surrounding tissue.

Mast cells differentiate from bone-marrow derived CD34+ myeloic precursor cells. After leaving the blood stream, these precursors differentiate under the influence of local growth factors to mature tissue mast cells (Wedemeyer et al. 2000, Curr Opin Immunol. 2000; 12(6):624-31). Mast cells reside in close proximity to vessels, nerves and surface epithelium. In human skin, the highest density of mast cells can be found around hair follicles, sweat glands, sebaceous glands and capillaries of the stratum papillare (Toruniowa, Jablonska 1988). Anatomical and functional interactions between mast cells and peripheral nerves have also been reported (Bienenstock et al. 1987 Int Arch Allergy Appl Immunol 82: 238-43; Naukkarinen et al. 1996. J Pathol. 1996; 180(2):200-5).

Mast cells have a diameter of 9-11 μm and are characterized by numerous basophilic granules. Mast cells are important effectors of allergic reactions. Mast cells play an important role in many physiological and pathological processes because of their susceptibility to numerous activating stimuli and their ability to release a plethora of different mediators. Mast cells have been implicated in numerous skin and mucosal diseases, including inflammation, hypersensitivity, and tissue repair (Benoist and Mathis, 2002; Nature. 2002; 420(6917):875-8). Mast cells communicate with sensory nerves and blood vessels via histamine release, thereby regulating neurogenic inflammation and pruritus (Steinhoff et al., 2003, Arch Dermatol. 2003; 139(11):1479-88.

Urticaria is a dermatological disease which involves activated mast cells. In urticarial lesions, mast cells are degranulated, and the effects of vasoactive mast cell components like histamine dominate the clinical symptoms. Many patients suffer from hives, pruritus and soft tissue swelling. The causes of urticaria are numerous, indeed, there are different entities ranging from acute urticaria as symptom of an allergic anaphylaxis, e.g. after ingestion of peanuts in a peanut allergic patient. Type I allergies are unique in this context because a specific mechanism and a specific agent are necessary to induce this effect. In other forms of urticaria, either specific triggers are unknown or do not exist (Maurer, et al., Hautarzt. 2003; 54(2):138-43). Urticaria may also occur in association with a viral or bacterial infection. Neuroendocrine factors are also known to be involved in the onset of e.g. adrenergic or cholinergic urticaria, both of which occur after physical exercise (Maurer et al., Hautarzt. 2004; 55(4):350-6; Mlynek et al., Curr Opin Allergy Clin Immunol. 2008; 8(5):433-7).

Typical treatment of urticaria involves blockage of histamine receptors of the H1 and, less commonly, the H2 subtype. Other pharmacological agents (such as cromoclycine acid or montelukast) have been reported to "stabilize" mast cell membranes; however, these agents have also been reported as less effective in the treatment of urticaria. Moreover, in severe cases, steroids need to be administered to prevent the onset of anaphylaxis.

One of the main drawbacks associated with current treatments for urticaria is the low efficacy of antihistamines in severe, life-threatening forms of acute urticaria and in the treatment of chronic forms of urticaria that do not have a determinable cause and are therefore referred to as idiopathic. Some patients suffer from idiopathic forms of urticaria for several years and have a strongly reduced quality of life (Mlynek et al., Curr Opin Allergy Clin Immunol. 2008; 8(5): 433-7).

Psoriasis is a polygenetic hereditary multifactorial inflammatory skin disease of complex pathogenesis, which may be influenced by a number of environmental factors. Despite substantial progress regarding the pathogenetic mechanisms involved in this disease, many factors still remain unresolved. Mast cells and macrophages are prominent in intial and developing psoriatic lesions, but are also found in stable lesions. Although late events leading to the clinical psoriatic phenotype are well understood (e.g., involvement of Th1 dominated cytokines leading to the epidermal psoriatic reaction pattern), early events which might unravel genetic alterations and crucial pathogenetic checkpoints remain obscure.

Several lines of evidence suggest an involvement of the cholinergic system in the pathogenesis of psoriasis. More than 50 years ago a Hungarian study group treated psoriasis patients with the anticholinergic substance atropine, based on the assumption that the parasympathetic nervous system must be responsible for an increased content of acetylcholine in the psoriatic lesions thus initiating the onset and mediating the course of the disease (Helmeczi, Dermatologica, 1955 110: 439-48). A careful analysis of the patients presented in Helmeczi's study reveals that almost exclusively those patients with "eruptive psoriasis" responded to the oral atropine treatment, while those with chronic plaque type psoriasis generally did not. According to several histological studies, the first cells that "arrive" in psoriasis lesions are mast cells and neutrophilic granulocytes. Indeed mast cells have been found significantly increased in number especially in guttate psoriasis and palmoplantar psoriasis (Schubert and Christophers, Arch Dermatol Res 1985; 277:352-8; Brody, J Invest Dermatol. 1984 May; 82(5):460-4; Naukkarinen et al., J Pathol. 1996 October; 180(2):200-5; Ashenagar et al., Arch Dermatol Res. 2007 February; 298(9):421-6) while chronic lesions are dominated by lymphocytes and macrophages (Ghoreschi K and Röcken M; J Dtsch Dermatol Ges 2003; 1: 524-32).

One study demonstrates a significant increase of mast cells in chronic psoriasis lesions only in patients complaining of pruritus (Nakamura et al. 2003 Br J Dermatol;149(4):718-30), while other immune cells and cytokines did not show any difference. In addition, mast cell degranulation has been shown to induce ICAM-1 expression in psoriatic epidermis, thus initiating the inflammatory cascade (Ackermann and Harvima, Arch Dermatol Res. 1998 July; 290(7):353-9). There is additional evidence for a role of mast cells in psoriasis from a mouse model. The so called flaky mouse (congenic fsn/fsn) shows diffuse epidermal orthokeratotic hyperkeratosis reminding strongly of psoriasis. In this mouse, numerous mast cells are lining up under the epidermis (Sundberg et al., Eur J Immunol 1998 April; 28(4):1379-88). The close "synapse-like" proximity of mast cells with free nerve endings containing a plethora of proinflammatory neurotransmitters together with their well-documented responsiveness to "stress-hormones" like CRH and urocortin, makes mast cells the ideal target for stress related and neurogenic inflammatory processes (Arck et al., J Mol. Med. 2005; 83(5): 386-96) which fits well to the clinical association of psoriasis with emotional stress (Singh et al., J Pharmacol Exp Ther. 1999 March; 288(3):1349-56). The physiological function of mast cells has been discussed intensely (Maurer et al., Exp Dermatol. 2003 December; 12(6):886-910); however, it has been convincingly demonstrated that mast cells are key cells of neuroendocrine inflammatory processes (Arck et al., J Mol. Med. 2005; 83(5):386-96; Siebenhaar, et al., J Allergy Clin Immunol. 2008; 121(4):955-61) that can be stimulated by a great variety of different stimuli, amongst them, acetylcholine (Fantozzi et al. 1978 Nature 273: 473-4).

There are several psoriasis treatment protocols aiming at secretory products of mast cells, in particular histamine. The use of H1-R and H2-R blockers has been suggested and documented in small studies (Kristensen et al., Br J. Dermatol. 1995 December; 133(6):905-8; Petersen et al., Acta Derm Venereol. 1998 May; 78(3):190-3); however, randomized controlled trials did not show significant therapeutic effects. These results/lack of effect may have been due to using the PASI score and not the psoriasis subtype or acuity as stratification factor (Zonneveld et al., J Am Acad Dermatol. 1997 June; 36(6 Pt 1):932-4. 7-103).

Several changes in the cholinergic system have been documented in psoriatic lesions: SLURP-2 is a peptide modulator of nicotinic cholinergic receptors that has been found elevated in psoriatic lesions. SLURP-2 has been shown to inhibit caspase-3 and filaggrin and, therefore, has been suggested to be involved in psoriasis through its role in keratinocyte hyperproliferation and/or T cell differentiation/activation (Tsuji et al., Genomics 2003; 81(1):26-33).

Smoking increases the risk of psoriasis at least in a subset of patients. This effect most probably is related to the main cigarette toxin, nicotine, a ligand of the nicotinic acetylcholine receptor (nAChR) (Arathi et al., Am J Med, 2007, 120 (11): 953-959) also active at the α10 nAChR present in mast cells. In addition, a special form of psoriasis, the pustulosis palmoplantaris (PPP) correlates strongly with smoking PPP lesions are particularly rich in mast cells expressing acetylcholine esterase (AChE) and granulocytes expressing ChAT and α3 nAChR. (Hagforsen et al., Acta Derm Venereol 2002; 82(5):341-6).

Mast cells are also key effector cells in bronchial asthma. Anticholinergic substances acting on the muscarinic acetylcholine receptor (mAChR) are on the market (tiotropium) for the treatment of asthma. It has been suggested that there may be an involvement of both neuronal and non-neuronal derived ACh in lung mucosal inflammation, involving lymphocytes and macrophages, mast cells (Wessler and Kirkpatrick, Pulm Pharmacol Ther. 2001; 14(6):423-34). This notion has immediate impact on the issue of tobacco-derived nicotine action in lung diseases on the one hand, and the use of anti-muscarinic drugs in chronic airway diseases on the other hand.

Rhinitis involves inflammation and swelling of the mucous membrane of the nose, characterized by a runny nose and stuffiness, and is usually caused by the common cold or an allergy.

Allergic rhinitis is the most common cause of rhinitis. It is an extremely common condition, affecting approximately 20% of the population. While allergic rhinitis is not a life-threatening condition, complications can occur and the condition can significantly impair quality of life, which leads to a number of indirect costs. The total direct and indirect cost of allergic rhinitis was recently estimated to be $5.3 billion per year.

Allergic rhinitis involves inflammation of the mucous membranes of the nose, eyes, eustachian tubes, middle ear, sinuses, and pharynx. The nose invariably is involved, and other organs are affected in certain individuals. Inflammation of the mucous membranes is characterized by a complex interaction of inflammatory mediators but ultimately is triggered by an immunoglobulin E (IgE)-mediated response to an extrinsic protein.

The tendency to develop allergic, or IgE-mediated, reactions to extrinsic allergens (proteins capable of causing an allergic reaction) has a genetic component. In susceptible individuals, exposure to certain foreign proteins leads to allergic sensitization, which is characterized by the production of specific IgE directed against these proteins. This specific IgE coats the surface of mast cells, which are present in the nasal mucosa. When the specific protein (e.g., a specific pollen grain) is inhaled into the nose, it can bind to the IgE on the mast cells, leading to immediate and delayed release of a number of mediators.

The mediators that are immediately released include histamine, tryptase, chymase, kinins, and heparin. The mast cells quickly synthesize other mediators, including leukotrienes and prostaglandin D2. These mediators, via various interactions, ultimately lead to the symptoms of rhinorrhea (ie, nasal congestion, sneezing, itching, redness, tearing, swelling, ear pressure, postnasal drip). Mucous glands are stimulated, leading to increased secretions. Vascular permeability is increased, leading to plasma exudation. Vasodilation occurs, leading to congestion and pressure. Sensory nerves are stimulated, leading to sneezing and itching. All of these events can occur in minutes; hence, this reaction is called the early, or immediate, phase of the reaction.

Over 4-8 hours, the above-mentioned mediators, through a complex interplay of events, lead to the recruitment of other inflammatory cells to the mucosa, such as neutrophils, eosinophils, lymphocytes, and macrophages. This results in continued inflammation, termed the late-phase response. The symptoms of the late-phase response are similar to those of the early phase, but less sneezing and itching and more congestion and mucus production tend to occur. The late phase may persist for hours or days.

Atopic dermatitis is a pruritic disease of unknown origin that usually starts in early infancy (an adult-onset variant is recognized); it is characterized by pruritus, eczematous lesions, xerosis (dry skin), and lichenification (thickening of the skin and an increase in skin markings). Atopic dermatitis may be associated with other atopic (immunoglobulin E [IgE]) diseases (e.g., asthma, allergic rhinitis, urticaria, acute allergic reactions to foods). Atopic dermatitis has enormous morbidity, and the incidence and prevalence appear to be increasing.

Substantial evidence indicates that genetic factors are important in the development of atopic dermatitis (AD), but the pathophysiology is still poorly understood. Two main hypotheses have been proposed regarding the development of the inflammatory lesions. The first suggests an immune dysfunction resulting in IgE sensitization and a secondary epithelial-barrier disturbance. The second proposes a defect in epithelial cells leading to the defective barrier problem, with the immunological aspects being epiphenomena.

Pruritus is a common manifestation of dermatologic diseases, such as urticaria, atopic dermatitis, and other allergic reactions. Effective treatment of pruritus can prevent scratch-induced complications such as lichen simplex chronicus and impetigo.

Pruritus originates within the skin's free nerve endings, which are most heavily concentrated in the wrists and ankles. The sensation of pruritus is transmitted through C fibers to the dorsal horn of the spinal cord and then to the cerebral cortex via the spinothalamic tract. Pruritus generates a spinal reflex response, the scratch, which is as innate as a deep tendon reflex. Regardless of the cause, pruritus often is exacerbated by skin inflammation, dry or hot ambient conditions, skin vasodilation, and psychologic stressors.

Histamine, which is released by mast cells in persons with urticaria and other allergic reactions, is one of the factors classically associated with pruritus.

As noted above, there are various disadvantages associated with the available treatments for mast cell mediated diseases such as urticaria, atopic dermatitis, psoriasis, pruritus, asthma, rhinitis, mastocytosis, conjunctivitis and keratoconjunctivitis. Thus, a need exists for improved treatments for urticaria, atopic dermatitis, psoriasis, pruritus, asthma, rhinitis, mastocytosis, conjunctivitis and keratoconjunctivitis and other mast cell mediated diseases.

1-Amino-alkylcyclohexane derivatives such as neramexane (also known as 1-amino-1,3,3,5,5-pentamethylcyclohexane) have been found to be useful in the therapy of various diseases especially in certain neurological diseases, including Alzheimer's disease and neuropathic pain. 1-Amino-alkylcyclohexane derivatives such as neramexane are disclosed in detail in U.S. Pat. Nos. 6,034,134 and 6,071,966, the subject matter of which patents is hereby incorporated by reference. It is believed that the therapeutic action of 1-amino-alkylcyclohexanes such as neramexane is related to the inhibition of the effects of excessive glutamate at the N-methyl-D-aspartate (NMDA) receptors of nerve cells, for which reason the compounds are also categorized as NMDA antagonists, or NMDA receptor antagonists.

Neramexane is also a blocker of the $\alpha 9\alpha 10$ nicotinic Acetylcholine Receptor. Neramexane behaves as a non-competitive antagonist. Since blockage by neramexane at concentrations higher than 1 mM has been reported to be only slightly dependent on the membrane potential and has also been reported not to modify the rate of desensitization, an additional mechanism might be involved. (Plazas, Paola V. et al., European Journal of Pharmacology 2007; 566: 11-19).

SUMMARY OF THE INVENTION

The present invention relates to a method of treating and/or preventing mast cell mediated diseases, such as urticaria, atopic dermatitis, psoriasis, pruritus, asthma, rhinitis, mastocytosis, conjunctivitis, and keratoconjunctivitis in a subject in need thereof, comprising administering to the individual an effective amount of a 1-amino-alkylcyclohexane derivative (e.g., neramexane or a pharmaceutically acceptable salt thereof such as neramexane mesylate).

The present invention also relates to a method of treating and/or preventing mast cell mediated diseases, such as food allergies in a subject in need thereof, comprising administering to the individual an effective amount of a 1-amino-alkylcyclohexane derivative (e.g., neramexane or a pharmaceutically acceptable salt thereof such as neramexane mesylate).

A further aspect of the invention relates to such a method wherein the 1-amino-alkylcyclohexane derivative (e.g., neramexane or a pharmaceutically acceptable salt thereof such as neramexane mesylate) is administered once a day, twice a day (b.i.d.), or three times a day.

A further aspect of the invention relates to such a method wherein the 1-amino-alkylcyclohexane derivative (e.g., neramexane or a pharmaceutically acceptable salt thereof such as neramexane mesylate) is administered in an immediate release formulation.

A further aspect of the invention relates to such a method wherein the 1-amino-alkylcyclohexane derivative (e.g., neramexane or a pharmaceutically acceptable salt thereof such as neramexane mesylate) is administered in a modified release formulation.

A further aspect of the invention relates to such a method wherein the 1-amino-alkylcyclohexane derivative (e.g., neramexane or a pharmaceutically acceptable salt thereof such as neramexane mesylate) is administered in a topical formulation such as a topical rinse off or leave on formulation.

A further aspect of the invention relates to such a method wherein the 1-amino-alkylcyclohexane derivative (e.g., neramexane or a pharmaceutically acceptable salt thereof such as neramexane mesylate) is administered in an oral formulation.

A further aspect of the invention relates to such a method wherein the 1-amino-alkylcyclohexane derivative (e.g., neramexane or a pharmaceutically acceptable salt thereof such as neramexane mesylate) is administered systemically.

A further aspect of the invention relates to a method of treating and/or preventing mast cell mediated diseases in a subject in need thereof, comprising administering to the individual an effective amount of a 1-amino-alkylcyclohexane derivative (e.g., neramexane or a pharmaceutically acceptable salt thereof such as neramexane mesylate) and one or more additional pharmaceutical agents (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) which has been shown to be effective in treating or preventing mast cell mediated diseases.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered conjointly.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered in a single formulation.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered in a topical formulation such as topical rinse-off or leave-on formulation.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) is administered systemically.

A further aspect of the invention relates to such a method wherein the 1-amino-alkylcyclohexane derivative (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered in an oral formulation.

A further aspect of the invention relates to a 1-amino-alkylcyclohexane derivative (e.g., neramexane or a pharmaceutically acceptable salt thereof such as neramexane mesylate) for the treatment of an individual afflicted with mast cell mediated diseases such as urticaria, atopic dermatitis, psoriasis, pruritus, asthma, rhinitis, mastocytosis, conjunctivitis, and keratoconjunctivitis.

A further aspect of the invention relates to a 1-amino-alkylcyclohexane derivative (e.g., neramexane or a pharmaceutically acceptable salt thereof such as neramexane mesylate) for the treatment of an individual afflicted with mast cell mediated diseases such as food allergies.

A further aspect of the invention relates to the use of a 1-amino-alkylcyclohexane derivative (e.g., neramexane or a pharmaceutically acceptable salt thereof such as neramexane mesylate) for the manufacture of a medicament for treatment of an individual afflicted with mast cell mediated diseases such as urticaria, atopic dermatitis, psoriasis, pruritus, asthma, rhinitis, mastocytosis, conjunctivitis, and keratoconjunctivitis.

A further aspect of the invention relates to the use of a 1-amino-alkylcyclohexane derivative (e.g., neramexane or a pharmaceutically acceptable salt thereof such as neramexane mesylate) for the manufacture of a medicament for treatment of an individual afflicted with mast cell mediated diseases such as food allergies.

A further aspect of the invention relates to the above-defined derivative or use wherein neramexane mesylate is administered in a range from about 5 mg to about 150 mg/day, or neramexane mesylate is administered in a range from about 5 mg to about 100 mg/day, or neramexane mesylate is administered in a range from about 5 mg to about 75 mg/day, or wherein neramexane mesylate is administered at about 50 mg/day or wherein neramexane mesylate is administered at about 75 mg/day for example in an oral formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered once a day, twice a day (b.i.d.), or three times a day.

A further aspect of the invention relates to the above-defined derivative or use wherein the 1-amino-alkylcyclohexane derivative (e.g., neramexane or a pharmaceutically acceptable salt thereof such as neramexane mesylate) is administered in an immediate release formulation or a modified release formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered in a topical formulation, such as a topical rinse off or leave on formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered in an oral formulation.

A further aspect of the invention relates to the above-defined derivative or use wherein the 1-amino-alkylcyclohexane derivative (e.g., neramexane or a pharmaceutically acceptable salt thereof such as neramexane mesylate) is administered systemically.

A further aspect of the invention relates to the above-defined derivative or use wherein at least one additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) which has been shown to be effective in treating or preventing mast cell mediated diseases is administered.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered conjointly.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered in a single formulation.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered in a topical formulation such as a topical rinse-off or leave-on formulation.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered in an oral formulation.

A further aspect of the invention relates to the above-defined derivative or use wherein the 1-amino-alkylcyclohexane derivative (e.g., neramexane or a pharmaceutically acceptable salt thereof such as neramexane mesylate) and the additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) are administered systemically.

A further aspect of the invention relates to a pharmaceutical composition for the treatment of mast cell mediated diseases comprising a therapeutically effective amount of a 1-amino-alkylcyclohexane derivative (e.g., neramexane or a pharmaceutically acceptable salt thereof such as neramexane mesylate), and, optionally, at least one pharmaceutically acceptable carrier or excipient.

A further aspect of the invention relates to a pharmaceutical composition for the treatment of mast cell mediated diseases comprising a therapeutically effective amount of a 1-amino-alkylcyclohexane derivative (e.g., neramexane or a pharmaceutically acceptable salt thereof such as neramexane mesylate) in an immediate or modified release formulation.

A further aspect of the invention relates to a pharmaceutical composition for the treatment of mast cell mediated diseases comprising a therapeutically effective amount of a 1-amino-alkylcyclohexane derivative (e.g., neramexane or a pharmaceutically acceptable salt thereof such as neramexane mesylate) in a topical formulation.

A further aspect of the invention relates to a pharmaceutical composition for the treatment of mast cell mediated diseases comprising a therapeutically effective amount of a 1-amino-alkylcyclohexane derivative (e.g., neramexane or a pharmaceutically acceptable salt thereof such as neramexane mesylate) in an oral formulation.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) which has been shown to be effective in treating mast cell mediated diseases and, optionally, at least one pharmaceutically acceptable carrier or excipient.

A further aspect of the invention relates to a pharmaceutical composition comprising a therapeutically effective amount of a 1-amino-alkylcyclohexane derivative (e.g., neramexane or a pharmaceutically acceptable salt thereof such as neramexane mesylate) in combination with at least one additional pharmaceutical agent (e.g. anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) which has been shown to be effective in treating mast cell mediated diseases and, optionally, at least one pharmaceutically acceptable carrier or excipient in the form of an topical or oral formulation.

A further aspect of the invention relates to a method of treating or preventing mast cell mediated diseases in a subject in need thereof, comprising administering an effective amount of a 1-amino-alkylcyclohexane derivative.

A further aspect of the invention relates to such a method wherein the 1-amino-alkylcyclohexane derivative is neramexane or a pharmaceutically acceptable salt thereof.

A further aspect of the invention relates to such a method wherein the 1-amino-alkylcyclohexane derivative is neramexane mesylate.

A further aspect of the invention relates to such a method wherein neramexane mesylate is administered in a range from about 5 mg to about 150 mg/day.

A further aspect of the invention relates to such a method wherein neramexane mesylate is administered in a range from about 5 mg to about 100 mg/day.

A further aspect of the invention relates to such a method wherein neramexane mesylate is administered at about 5 mg to about 75 mg/day.

A further aspect of the invention relates to such a method wherein neramexane mesylate is administered at about 50 mg/day.

A further aspect of the invention relates to such a method wherein neramexane mesylate is administered at about 75 mg/day.

A further aspect of the invention relates to a method of treating or preventing mast cell mediated diseases in a subject in need thereof, comprising administering an effective amount of a 1-amino-alkylcyclohexane derivative, wherein the 1-amino-alkylcyclohexane derivative is administered once a day, twice a day (b.i.d.), or three times a day.

A further aspect of the invention relates to a method of treating or preventing mast cell mediated diseases in a subject in need thereof, comprising administering an effective amount of a 1-amino-alkylcyclohexane derivative, wherein the 1-amino-alkylcyclohexane derivative is administered in a topical formulation.

A further aspect of the invention relates to such a method wherein the 1-amino-alkylcyclohexane derivative is administered between 0.1 and 99% by weight of the formulation.

A further aspect of the invention relates to a method of treating or preventing mast cell mediated diseases in a subject in need thereof, comprising administering an effective amount of a 1-amino-alkylcyclohexane derivative, wherein the 1-amino-alkylcyclohexane derivative is administered in an oral formulation.

A further aspect of the invention relates to a method of treating or preventing mast cell mediated diseases, wherein the mast cell mediated disease is not psoriasis, in a subject in need thereof, comprising administering an effective amount of a 1-amino-alkylcyclohexane derivative.

A further aspect of the invention relates to a method of treating or preventing a mast cell mediated disease selected from urticaria, atopic dermatitis, psoriasis, pruritus, asthma, rhinitis, mastocytosis, conjunctivitis and keratoconjunctivitis in a subject in need thereof, comprising administering an effective amount of a 1-amino-alkylcyclohexane derivative.

A further aspect of the invention relates to a method of treating or preventing atopic dermatitis in a subject in need thereof, comprising administering an effective amount of a 1-amino-alkylcyclohexane derivative.

A further aspect of the invention relates to a method of treating or preventing a food allergy in a subject in need thereof, comprising administering an effective amount of a 1-amino-alkylcyclohexane derivative.

A further aspect of the invention relates to a method of treating or preventing a mast cell mediated disease selected from urticaria, atopic dermatitis, psoriasis, pruritus, asthma, rhinitis, mastocytosis, conjunctivitis and keratoconjunctivitis in a subject in need thereof, comprising administering an effective amount of a 1-amino-alkylcyclohexane derivative, wherein the 1-amino-alkylcyclohexane derivative is administered in a topical formulation.

A further aspect of the invention relates to a pharmaceutical composition comprising a therapeutically effective amount of a 1-amino-alkylcyclohexane derivative in combination with an additional pharmaceutical agent which has been shown to be effective for the treatment or the prevention of mast cell mediated diseases and, optionally, at least one pharmaceutically acceptable carrier or excipient.

A further aspect of the invention relates to such a pharmaceutical composition wherein the 1-amino-alkylcyclohexane derivative is neramexane or a pharmaceutically acceptable salt thereof.

BRIEF DESCRIPTION OF THE DRAWINGS

FIG. 1 shows the effects of neramexane on mast cell degranulation in vitro.

DETAILED DESCRIPTION OF THE INVENTION

As used herein, the term mast cell mediated diseases includes urticaria, atopic dermatitis, psoriasis, pruritus, asthma, rhinitis, mastocytosis, conjunctivitis, and keratoconjunctivitis.

As used herein, the term mast cell mediated diseases includes also food allergies.

As used herein, the term urticaria includes allergic urticaria and non-allergic urticaria.

As used herein, the term atopic dermatitis includes atopic eczema

As used herein, the term psoriasis includes psoriasis vulgaris, plaque psoriasis, flexural psoriasis, inverse psoriasis, guttate psoriasis, pustular psoriasis, nail psoriasis, erythrodermic psoriasis and psoriatic arthritis.

As used herein, the term asthma includes asthma bronchiale, allergic and non-allergic asthma.

As used herein, the term rhinitis includes allergic rhinitis (e.g seasonal, perennial, and occupational rhinitis) and non allergic rhinitis (e.g. eosinophils, autonomic, hormonal, drug-induced, atrophic, and gustatory rhinitis) and infective rhinitis.

As used herein, the term mastocytosis includes cutaneous mastocytosis and systemic mastocytosis.

As used herein, the term food allergy includes an immune response to a food protein such as a dairy allergy, an egg allergy, a peanut allergy, a tree nut allergy, a seafood allergy, a shellfish allergy, a soy allergy, and a wheat allergy or a combination thereof.

As used herein, the terms mecamylamine, kynurenic acid, d-tubocurarine, hexamethonium, atropine, ipratropium, oxitropium, tiotropium, Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil, prednisone, cortisone, hydrocortisone, ciclesonide, beclomethasone, budesonide, flunisolide, fluticasone, mometasone, triamcinolone, montelukast, zafirlukast, pranlukast, zileuton, Methylxanthines, theophylline, aminophylline, Omalizumab, Methotrexate, and ketotifen include optical isomers, diastereomers, enantiomers, hydrates, pharmaceutically acceptable salts, and mixtures thereof, respectively.

As used herein, the term "subject" encompasses mammals including animals and humans.

The term 1-amino-alkylcyclohexane derivative is used herein to describe a 1-amino-alkylcyclohexane or a compound derived from 1-amino-alkylcyclohexane, e.g., pharmaceutically acceptable salts of 1-amino-alkylcyclohexanes.

The 1-amino-alkylcyclohexane derivatives of the present invention may be represented by the general formula (I):

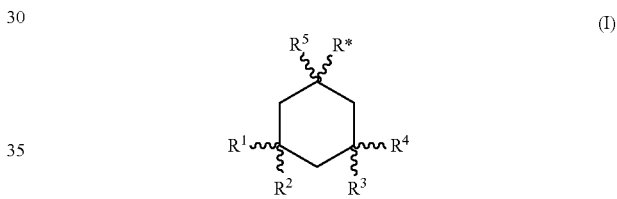

wherein R* is —$(CH_2)_n$—$(CR^6R^7)_m$—$NR^8R^9$
wherein n+m=0, 1, or 2
wherein $R^1$ through $R^7$ are independently selected from the group consisting of hydrogen and $C_{1-6}$alkyl, wherein $R^8$ and $R^9$ are independently selected from the group consisting of hydrogen and $C_{1-6}$alkyl or together represent lower-alkylene —$(CH_2)_x$— wherein x is 2 to 5, inclusive, and optical isomers, enantiomers, hydrates, and pharmaceutically-acceptable salts thereof.

Non-limiting examples of the 1-amino-alkylcyclohexanes used according to the present invention include:
1-amino-1,3,5-trimethylcyclohexane,
1-amino-1(trans),3(trans),5-trimethylcyclohexane,
1-amino-1(cis),3(cis),5-trimethylcyclohexane,
1-amino-1,3,3,5-tetramethylcyclohexane,
1-amino-1,3,3,5,5-pentamethylcyclohexane (neramexane),
1-amino-1,3,5,5-tetramethyl-3-ethylcyclohexane,
1-amino-1,5,5-trimethyl-3,3-diethylcyclohexane,
1-amino-1,5,5-trimethyl-cis-3-ethylcyclohexane,
1-amino-(1S,5S)cis-3-ethyl-1,5,5-trimethylcyclohexane,
1-amino-1,5,5-trimethyl-trans-3-ethylcyclohexane,
1-amino-(1R,5S)trans-3-ethyl-1,5,5-trimethylcyclohexane,
1-amino-1-ethyl-3,3,5,5-tetramethylcyclohexane,
1-amino-1-propyl-3,3,5,5-tetramethylcyclohexane,
N-methyl-1-amino-1,3,3,5,5-pentamethylcyclohexane,
N-ethyl-1-amino-1,3,3,5,5-pentamethyl-cyclohexane,
N-(1,3,3,5,5-pentamethylcyclohexyl)pyrrolidine,
3,3,5,5-tetramethylcyclohexylmethylamine,
1-amino-1-propyl-3,3,5,5-tetramethylcyclohexane, 1 amino-1,3,3,5(trans)-tetramethylcyclohexane (axial amino group),
3-propyl-1,3,5,5-tetramethylcyclohexylamine semihydrate,
1-amino-1,3,5,5-tetramethyl-3-ethylcyclohexane,
1-amino-1,3,5-trimethylcyclohexane,
1-amino-1,3-dimethyl-3-propylcyclohexane,
1-amino-1,3(trans),5(trans)-trimethyl-3(cis)-propylcyclohexane,
1-amino-1,3-dimethyl-3-ethylcyclohexane,
1-amino-1,3,3-trimethylcyclohexane,
cis-3-ethyl-1(trans)-3(trans)-5-trimethylcyclohexamine,
1-amino-1,3(trans)-dimethylcyclohexane,
1,3,3-trimethyl-5,5-dipropylcyclohexylamine,
1-amino-1-methyl-3(trans)-propylcyclohexane,
1-methyl-3(cis)-propylcyclohexylamine,
1-amino-1-methyl-3(trans)-ethylcyclohexane,
1-amino-1,3,3-trimethyl-5(cis)-ethylcyclohexane,
1-amino-1,3,3-trimethyl-5(trans)-ethylcyclohexane,
cis-3-propyl-1,5,5-trimethylcyclohexylamine,
trans-3-propyl-1,5,5-trimethylcyclohexylamine,
N-ethyl-1,3,3,5,5-pentamethylcyclohexylamine,
N-methyl-1-amino-1,3,3,5,5-pentamethylcyclohexane,
1-amino-1-methylcyclohexane,
N,N-dimethyl-1-amino-1,3,3,5,5-pentamethylcyclohexane,
2-(3,3,5,5-tetramethylcyclohexyl)ethylamine,
2-methyl-1-(3,3,5,5-tetramethylcyclohexyl)propyl-2-amine,
2-(1,3,3,5,5-pentamethylcyclohexyl-1)-ethylamine semihydrate,
N-(1,3,3,5,5-pentamethylcyclohexyl)-pyrrolidine,
1-amino-1,3(trans),5(trans)-trimethylcyclohexane,
1-amino-1,3(cis),5(cis)-trimethylcyclohexane,
1-amino-(1R,5S)trans-5-ethyl-1,3,3-trimethylcyclohexane,
1-amino-(1S,5S)cis-5-ethyl-1,3,3-trimethylcyclohexane,
1-amino-1,5,5-trimethyl-3(cis)-isopropyl-cyclohexane,
1-amino-1,5,5-trimethyl-3(trans)-isopropyl-cyclohexane,
1-amino-1-methyl-3(cis)-ethyl-cyclohexane,
1-amino-1-methyl-3(cis)-methyl-cyclohexane,
1-amino-5,5-diethyl-1,3,3-trimethyl-cyclohexane,
1-amino-1,3,3,5,5-pentamethylcyclohexane,
1-amino-1,5,5-trimethyl-3,3-diethylcyclohexane,
1-amino-1-ethyl-3,3,5,5-tetramethylcyclohexane,
N-ethyl-1-amino-1,3,3,5,5-pentamethylcyclohexane,
N-(1,3,5-trimethylcyclohexyl)pyrrolidine or piperidine,
N-[1,3(trans),5(trans)-trimethylcyclohexyl]pyrrolidine or piperidine,
N-[1,3(cis),5(cis)-trimethylcyclohexyl]pyrrolidine or piperidine,
N-(1,3,3,5-tetramethylcyclohexyl)pyrrolidine or piperidine,
N-(1,3,3,5,5-pentamethylcyclohexyl)pyrrolidine or piperidine,
N-(1,3,5,5-tetramethyl-3-ethylcyclohexyl)pyrrolidine or piperidine,
N-(1,5,5-trimethyl-3,3-diethylcyclohexyl)pyrrolidine or piperidine,
N-(1,3,3-trimethyl-cis-5-ethylcyclohexyl)pyrrolidine or piperidine,
N-[(1S,5S)cis-5-ethyl-1,3,3-trimethylcyclohexyl]pyrrolidine or piperidine,
N-(1,3,3-trimethyl-trans-5-ethylcyclohexyl)pyrrolidine or piperidine,
N-[(1R,5S)trans-5-ethyl,3,3-trimethylcyclohexyl]pyrrolidine or piperidine,
N-(1-ethyl-3,3,5,5-tetramethylyclohexyl)pyrrolidine or piperidine,
N-(1-propyl-3,3,5,5-tetramethylcyclohexyl)pyrrolidine or piperidine,
N-(1,3,3,5,5-pentamethylcyclohexyl)pyrrolidine,
and optical isomers, diastereomers, enantiomers, hydrates, their pharmaceutically acceptable salts, and mixtures thereof.

1-Amino-alkylcyclohexane derivatives (e.g., neramexane, 1-amino-1,3,3,5,5-pentamethylcyclohexane) are disclosed in U.S. Pat. Nos. 6,034,134 and 6,071,966. 1-Amino-alkylcyclohexane derivatives (e.g., neramexane) may be used according to the invention in the form of any of pharmaceutically acceptable salts, solvates, isomers, conjugates, and prodrugs, any references to 1-amino-alkylcyclohexane derivatives (e.g., neramexane) in this description should be understood as also referring to such salts, solvates, isomers, conjugates, and prodrugs.

Pharmaceutically acceptable salts include, but are not limited to, acid addition salts, such as those made with hydrochloric, methylsulfonic, hydrobromic, hydroiodic, perchloric, sulfuric, nitric, phosphoric, acetic, propionic, glycolic, lactic, pyruvic, malonic, succinic, fumaric, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicylic, p-aminosalicylic, 2-phenoxybenzoic, and 2-acetoxybenzoic acid. All of these salts (or other similar salts) may be prepared by conventional means. The nature of the salt is not critical, provided that it is non-toxic and does not substantially interfere with the desired pharmacological activity.

The term "analog" or "derivative" is used herein in the conventional pharmaceutical sense, to refer to a molecule that structurally resembles a reference molecule (such as neramexane), but has been modified in a targeted and controlled manner to replace one or more specific substituents of the reference molecule with an alternate substituent, thereby generating a molecule which is structurally similar to the reference molecule. Synthesis and screening of analogs (e.g., using structural and/or biochemical analysis), to identify slightly modified versions of a known compound which may have improved or biased traits (such as higher potency and/or selectivity at a specific targeted receptor type, greater ability to penetrate mammalian barriers, such as cell membranes, fewer side effects, etc.) is a drug design approach that is well known in pharmaceutical chemistry.

The term "treat" is used herein to mean to relieve or alleviate at least one symptom of a disease in a subject. Within the meaning of the present invention, the term "treat" also denotes to arrest, delay the onset (i.e., the period prior to clinical manifestation of a disease) and/or reduce the risk of developing or worsening a disease.

The term "therapeutically effective" applied to dose or amount refers to that quantity of a compound or pharmaceutical composition that is sufficient to result in a desired activity upon administration to a mammal in need thereof.

The phrase "pharmaceutically acceptable", as used in connection with compositions of the invention, refers to molecular entities and other ingredients of such compositions that are physiologically tolerable and do not typically produce untoward reactions when administered to a mammal (e.g., human). The term "pharmaceutically acceptable" may also mean approved by a regulatory agency of the Federal or a state government or listed in the U.S. Pharmacopeia or other generally recognized pharmacopeia for use in mammals, and more particularly in humans.

The term "carrier" applied to pharmaceutical compositions of the invention refers to a diluent, excipient, or vehicle with which an active compound (e.g., neramexane) is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical carriers are described e.g. in "Remington's Pharmaceutical Sciences" by A. R. Gennaro, 20$^{th}$ Edition.

The term "about" or "approximately" usually means within 20%, alternatively within 10%, including within 5% of a given value or range. Alternatively, especially in biological systems, the term "about" means within about a log (i.e., an order of magnitude), including within a factor of two of a given value.

Pharmaceutical Formulations and Administration

In conjunction with the methods of the present invention, also provided are pharmaceutical compositions comprising a therapeutically effective amount of a 1-amino-alkylcyclohexane derivative (e.g., neramexane). The compositions of the invention may further comprise a carrier or excipient (all pharmaceutically acceptable). The compositions may be formulated for once-a-day administration, twice-a-day administration, or three times a day administration.

The active ingredient (e.g., neramexane, such as neramexane mesylate) or the composition of the present invention may be used for the treatment of at least one of the mentioned disorders, wherein the treatment is adapted to or appropriately prepared for a specific administration as disclosed herein (e.g., to once-a-day, twice-a-day, or three times a day administration). For this purpose the package leaflet and/or the patient information contains corresponding information.

The active ingredient (e.g., neramexane, such as neramexane mesylate) or the composition of the present invention may be used for the manufacture of a medicament for the treatment of at least one of the mentioned disorders, wherein the medicament is adapted to or appropriately prepared for a specific administration as disclosed herein (e.g., to once-a-day, twice-a-day, or three times a day administration). For this purpose the package leaflet and/or the patient information contains corresponding information.

According to the present invention, the dosage form of the 1-amino-alkylcyclohexane derivative (e.g., neramexane) may be a solid, semisolid, or liquid formulation according to the following.

The 1-amino-alkylcyclohexane derivatives of the present invention (e.g., neramexane) may be administered orally, topically, parenterally, or mucosally (e.g., buccally, by inhalation, or rectally) in dosage unit formulations containing conventional non-toxic pharmaceutically acceptable carriers. In another embodiment for administration to pediatric subjects, the 1-amino-alkylcyclohexane derivative may be formulated as a flavored liquid (e.g., peppermint flavor). The 1-amino-alkylcyclohexane derivatives of the present invention may be administered orally in the form of a capsule, a tablet, or the like, or as a liquid formulation or topically as a semi-solid such as an ointment, cream, gel, or hydrogel (see Remington's Pharmaceutical Sciences, 20$^{th}$ Edition, by A. R. Gennaro).

For oral administration in the form of a tablet or capsule, the 1-amino-alkylcyclohexane derivatives of the present invention (e.g., neramexane) may be combined with non-toxic, pharmaceutically acceptable excipients such as binding agents (e.g., pregelatinized maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulfate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), coloring and flavoring agents, gelatin, sweeteners, natural and synthetic gums (such as acacia, tragacanth or alginates), buffer salts, carboxymethylcellulose, polyethyleneglycol, waxes, and the like.

The tablets may be coated with a concentrated sugar solution which may contain e.g., gum arabic, gelatine, talcum, titanium dioxide, and the like. Alternatively, the tablets can be coated with a polymer that dissolves in a readily volatile organic solvent or mixture of organic solvents. In specific embodiments, neramexane is formulated in immediate-release (IR) or modified-release (MR) dosage forms. Immediate release solid dosage forms permit the release of most or all of the active ingredient over a short period of time, such as 60 minutes or less, and make rapid absorption of the drug possible (immediate release formulations of 1-amino-alkylcyclohexanes such as neramexane are disclosed in US Published Application Nos. 2006/0002999 and 2006/0198884, the subject matter of which is hereby incorporated by reference). Modified release solid oral dosage forms permit the sustained release of the active ingredient over an extended period of time in an effort to maintain therapeutically effective plasma levels over similarly extended time intervals and/or to modify other pharmacokinetic properties of the active ingredient (modified release formulations of neramexane are disclosed in US Published Application No. 2007/0141148, the subject matter of which is hereby incorporated by reference).

For the formulation of soft gelatin capsules, the 1-amino-alkylcyclohexane derivatives of the present invention (e.g., neramexane) may be admixed with e.g., a vegetable oil or poly-ethylene glycol. Hard gelatin capsules may contain granules of the active substances using either the above mentioned excipients for tablets e.g., lactose, saccharose, sorbitol, mannitol, starches (e.g., potato starch, corn starch or amylopectin), cellulose derivatives or gelatine. Also liquids or semisolids of the drug can be filled into hard gelatine capsules.

The 1-amino-alkylcyclohexane derivatives of the present invention (e.g., neramexane) can also be introduced in microspheres or microcapsules, e.g., fabricated from polyglycolic acid/lactic acid (PGLA) (see, e.g., U.S. Pat. Nos. 5,814,344; 5,100,669 and 4,849,222; PCT Publications No. WO 95/11010 and WO 93/07861). Biocompatible polymers may be used in achieving controlled release of a drug, include for example, polylactic acid, polyglycolic acid, copolymers of polylactic and polyglycolic acid, polyepsilon caprolactone, polyhydroxybutyric acid, polyorthoesters, polyacetals, polyhydropyrans, polycyanoacrylates, and cross-linked or amphipathic block copolymers of hydrogels.

Formulation of the 1-amino-alkylcyclohexane derivatives of the present invention in a semi-solid or liquid form may also be used. The 1-amino-alkylcyclohexane derivative (e.g., neramexane) may constitute between 0.1 and 99% by weight of the formulation, more specifically between 0.5 and 20% by weight for formulations intended for injection and between 0.2 and 50% by weight for formulations suitable for oral administration.

Formulations of the 1-amino-alkylcyclohexane derivatives of the present invention in a semi-solid or liquid form suitable for topical administration may also be used. Such formulations include gels, creams, ointments, hydrogels, pastes, emulsions, sprays, solutions, lotions, etc. The 1-amino-alkylcyclohexane derivative (e.g., neramexane) may constitute between 0.1 and 99% by weight of the formulation, more specifically between 0.5% and 50% by weight of the formulation or between 1% and 25% by weight of the formulation or between 2% and 20% by weight of the formulation.

In one embodiment of the invention, the 1-amino-alkylcyclohexane derivative (e.g., neramexane) is administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

A modified release form dosage form may comprise a core either coated with or containing a drug. The core is then coated with a release modifying polymer within which the drug is dispersed. The release modifying polymer disintegrates gradually, releasing the drug over time. Thus, the outermost layer of the composition effectively slows down and thereby regulates the diffusion of the drug across the coating layer when the composition is exposed to an aqueous environment, i.e. the gastrointestinal tract. The net rate of diffusion of the drug is mainly dependent on the ability of the gastric fluid to penetrate the coating layer or matrix and on the solubility of the drug itself.

In another embodiment of the invention, the 1-amino-alkylcyclohexane derivative (e.g., neramexane) is formulated in an oral, liquid formulation. Liquid preparations for oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound. Oral liquid formulations of 1-amino-alkylcyclohexanes, such as neramexane, are described in PCT International Application No. PCT/US2004/037026, the subject matter of which is hereby incorporated by reference.

For oral administration in liquid form, 1-amino-alkylcyclohexane derivatives of the present invention (e.g., neramexane) may be combined with non-toxic, pharmaceutically acceptable inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. Stabilizing agents such as antioxidants (e.g. BHA, BHT, propyl gallate, sodium ascorbate, citric acid) can also be added to stabilize the dosage forms. For example, solutions may contain from about 0.2% to about 20% by weight of neramexane, with the balance being sugar and mixture of ethanol, water, glycerol and propylene glycol. Optionally, such liquid formulations may contain coloring agents, flavoring agents, sweetening agents and thickening agents, such as carboxymethyl-cellulose, or other excipients.

In another embodiment, a therapeutically effective amount of a 1-amino-alkylcyclohexane derivative (e.g., neramexane) is administered in an oral solution containing a preservative, a sweetener, a solubilizer, and a solvent. The oral solution may include one or more buffers, flavorings, or additional excipients. In a further embodiment, a peppermint or other flavoring is added to the neramexane derivative oral liquid formulation.

For administration by inhalation, 1-amino-alkylcyclohexane derivatives (e.g., neramexane) of the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

Solutions for parenteral applications by injection may be prepared in an aqueous solution of a water-soluble pharmaceutically acceptable salt of the active substances, for example in a concentration of from about 0.5% to about 10% by weight. These solutions may also contain stabilizing agents and/or buffering agents and may conveniently be provided in various dosage unit ampoules.

The formulations of the invention may be delivered parenterally, i.e., by intravenous (i.v.), intracerebroventricular (i.c.v.), subcutaneous (s.c.), intraperitoneal (i.p.), intramuscular (i.m.), subdermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. Alternatively, the active ingredient may be in powder form for reconstitution with a suitable vehicle, e.g., sterile pyrogen-free water, before use.

The invention also provides a pharmaceutical pack or kit comprising one or more containers containing a 1-amino-alkylcyclohexane derivative (e.g., neramexane) and, optionally, more of the ingredients of the formulation. In a specific embodiment, neramexane is provided as an oral solution (2 mg/ml) for administration with the use of a 2 teaspoon capacity syringe (dosage KORC®). Each oral syringe has hatch marks for measurement, with lines on the right side of the syringe (tip down) representing tsp units, and those on the left representing ml units.

The optimal therapeutically effective amount may be determined experimentally, taking into consideration the exact mode of administration, from in which the drug is administered, the indication toward which the administration is directed, the subject involved (e.g., body weight, health, age, sex, etc.), and the preference and experience of the physician or veterinarian in charge.

Dosage units for rectal application may be solutions or suspensions or may be prepared in the form of suppositories or retention enemas comprising neramexane in a mixture with a neutral fatty base, or gelatin rectal capsules comprising the active substances in admixture with vegetable oil or paraffin oil.

Toxicity and therapeutic efficacy of the compositions of the invention may be determined by standard pharmaceutical procedures in experimental animals, e.g., by determining the $LD_{50}$ (the dose lethal to 50% of the population) and the $ED_{50}$ (the dose therapeutically effective in 50% of the population). The dose ratio between therapeutic and toxic effects is the therapeutic index and it may be expressed as the ratio $LD_{50}/ED_{50}$. Compositions that exhibit large therapeutic indices are preferred.

Suitable daily doses of the active compounds of the invention in therapeutic treatment of humans are about 0.01-10 mg/kg bodyweight on peroral administration and 0.001-10 mg/kg bodyweight on parenteral administration. For example, for adults, suitable daily doses of neramexane (e.g. neramexane mesylate) are within the range from about 5 mg to about 150 mg per day, such as from about 5 mg to about 120 mg, from about 5 mg to about 100 mg, or from about 5 mg to about 75 mg, or from about 5 mg to about 50 mg, such as 25 mg or 37.5 mg or 50 mg, per day. For example the daily dose may be body weight-adjusted such as 50 mg/day up to 90 kg body weight or 75 mg/day for patients with a body weight of 90 kg. An equimolar amount of another pharmaceutically acceptable salt, a solvate, an isomer, a conjugate, a prodrug or a derivative thereof, such as neramexane hydrochloride, is also suitable. For pediatric subjects aged 4-14, neramexane (e.g. neramexane mesylate) may be administered as an oral, liquid dosage form, at about 0.5 mg/day, up to a maximum dose of 10 mg/day.

The daily doses indicated herein may be administered, for example, as one or two dosing units once, twice or three times per day. Suitable doses per dosage unit may therefore be the daily dose divided (for example, equally) between the number of dosage units administered per day, and will thus typically be about equal to the daily dose or one half, one third, one quarter or one sixth thereof. Dosages per dosage unit may thus be calculated from each daily dosage indicated herein. A daily dose of 5 mg, for example may be seen as providing a dose per dosage unit of, for example, about 5 mg, 2.5 mg, 1.67 mg, 1.25 mg and 0.83 mg, depending upon the dosing regimen chosen. Correspondingly, a dosage of 150 mg per day corresponds to dosages per dosing unit of, for example, about 150 mg, 75 mg, 50 mg, 37.5 mg, and 25 mg for corresponding dosing regimens.

Treatment duration may be short-term, e.g., several weeks (for example 8-14 weeks), or long-term until the attending physician deems further administration no longer is necessary.

The 1-amino-alkylcyclohexane derivatives of the present invention (e.g., neramexane) may be administered as a monotherapy, or in combination with another agent prescribed for the treatment of mast cell mediated diseases.

The term "combination" applied to active ingredients is used herein to define a single pharmaceutical composition (formulation) comprising two active agents (e.g., a pharmaceutical composition comprising a 1-amino-alkylcyclohexane derivative, such as neramexane, and another agent prescribed for the treatment of mast cell mediated diseases, such as anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) or two separate pharmaceutical compositions, each comprising an active agent (e.g. a pharmaceutical composition comprising a 1-amino-alkylcyclohexane derivative, such as neramexane, and another pharmaceutical composition comprising another agent prescribed for the treatment of mast cell mediated diseases, such as anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen), to be administered conjointly.

Within the meaning of the present invention, the term "conjoint administration" is used to refer to administration of 1-amino-alkylcyclohexane derivative, such as neramexane, and one or more additional active agents (e.g. another agent prescribed for the treatment of mast cell mediated diseases such as anticholinergic substances (e.g. mecamylamine, kynurenic acid, d-tubocurarine, hexamethonium, atropine, ipratropium, oxitropium, and tiotropium), antihistamines, (e.g. Diphenhydramine, Loratadine, Desloratadine, Meclizine, Quetiapine, Fexofenadine, Pheniramine, Cetirizine, Promethazine, Cimetidine, Famotidine, Ranitidine, Nizatidine, A-349,821, ABT-239, Ciproxifan, Clobenpropit, Thioperamide, JNJ 7777120, Cromoglicate, Nedocromil), Corticosteroids (e.g. prednisone, cortisone, hydrocortisone), glucocorticoids (e.g. ciclesonide, beclomethasone, budesonide, flunisolide, fluticasone, mometasone, and triamcinolone), Leukotriene modifiers (e.g. montelukast, zafirlukast, pranlukast, and zileuton), Methylxanthines (e.g. theophylline and aminophylline), Omalizumab, Methotrexate and ketotifen) simultaneously in one composition, or simultaneously in different compositions, or sequentially. For the sequential administration to be considered "conjoint", however, 1-amino-alkylcyclohexane derivative, such as neramexane, and the one or more additional agents must be administered separated by a time interval which still permits the resultant beneficial effect for treating mast cell mediated diseases in a mammal.

Examples of Representative Formulations

With the aid of commonly used solvents, auxiliary agents and carriers, active ingredients may be processed into tablets, coated tablets, capsules, drip solutions, suppositories, injection and infusion preparations, gels, creams, ointments, and the like and can be therapeutically applied by the oral, rectal, parenteral, topical, and additional routes. Tablets suitable for oral administration may be prepared by conventional tabletting techniques. The following example is given by way of illustration only and is not to be construed as limiting.

Formulation Example 1

Neramexane Mesylate Immediate Release Tablets

The following tables provide the make-up of neramexane immediate release tablets in 12.5, 25.0, 37.5, and 50.0 mg dosages, including active components, coating agents, and other excipients.

TABLE 1

Neramexane mesylate, 12.5 mg film coated tablets

| Component | Amount [mg] | Function |
|---|---|---|
| Neramexane mesylate | 12.50 | Active pharmaceutical ingredient |
| Cellulose microcrystalline | 103.25 | Binder |
| Croscarmellose sodium | 6.25 | Disintegrant |
| Silicon dioxide, colloidal | 1.25 | Flow promoter |
| Talc | 1.25 | Glident |
| Magnesium stearate | 0.50 | Lubricant |
| core weight | 125.00 | |
| Coating (HPMC), Opadry or Sepifilm | 5.00 | Coating |
| Coat weight | 5.00 | |
| coated tablet total weight | 130.00 | |

TABLE 2

Neramexane mesylate, 25.0 mg film coated tablets

| Component | Amount [mg] | Function |
|---|---|---|
| Neramexane mesylate | 25.00 | Active pharmaceutical ingredient |
| Cellulose microcrystalline | 206.50 | Binder |
| Croscarmellose sodium | 12.5 | Disintegrant |
| Silicon dioxide, colloidal | 2.50 | Flow promoter |
| Talc | 2.50 | Glident |
| Magnesium stearate | 1.00 | Lubricant |
| core weight | 250.00 | |
| Coating (HPMC), Opadry or Sepifilm | 10.00 | Coating |
| Coat weight | 10.00 | |
| coated tablet total weight | 260.00 | |

TABLE 3

Neramexane mesylate, 37.5 mg film coated tablets

| Component | Amount [mg] | Function |
|---|---|---|
| Neramexane mesylate | 37.50 | Active pharmaceutical ingredient |
| Cellulose microcrystalline | 309.75 | Binder |
| Croscarmellose sodium | 18.75 | Disintegrant |
| Silicon dioxide, colloidal | 3.75 | Flow promoter |
| Talc | 3.75 | Glident |
| Magnesium stearate | 1.50 | Lubricant |
| core weight | 375.00 | |
| Coating (HPMC), Opadry or Sepifilm | 15.00 | Coating |
| Coat weight | 15.00 | |
| coated tablet total weight | 390.00 | |

TABLE 4

Neramexane mesylate, 50.0 mg film coated tablets

| Component | Amount [mg] | Function |
|---|---|---|
| Neramexane mesylate | 50.00 | Active pharmaceutical ingredient |
| Cellulose microcrystalline | 413.00 | Binder |
| Croscarmellose sodium | 25.00 | Disintegrant |
| Silicon dioxide, colloidal | 5.00 | Flow promoter |
| Talc | 5.00 | Glident |
| Magnesium stearate | 2.00 | Lubricant |
| core weight | 500.00 | |
| Coating (HPMC), Opadry or Sepifilm | 20.00 | Coating |
| Coat weight | 20.00 | |
| coated tablet total weight | 520.00 | |

The following tables provide the make-up of Neramexane topical formulations.

Formulation Example 2

TABLE 5

"Unguentum emulsificans"

| Description | Amount |
|---|---|
| Alcohol cetylicus et stearylicus emulsificans | 30.0 g |
| Paraffinum subliquidum | 35.0 g |
| Vaselinum album | 35.0 g |

TABLE 6

"Unguentum emulsificans aquosum" containing 1% Neramexane

| Description | Amount |
|---|---|
| Neramexane mesylate | 1.0 g |
| Unguentum emulsificans | 30.0 g |
| Aqua purificata | 69.0 g |

TABLE 7

"Unguentum emulsificans aquosum" containing 20% Neramexane

| Description | Amount |
|---|---|
| Neramexane mesylate | 20.0 g |
| Unguentum emulsificans | 30.0 g |
| Aqua purificata | 50.0 g |

Formulation Example 3

TABLE 8

"Cremor nonionicus emulsificans aquosum"

| Description | Amount |
|---|---|
| Alcohol cetylicus et stearylicus emulsificans nonionicum | 21.0 g |
| 2-Ethylhexylis lauras | 10.0 g |
| Glycerolum 85% | 5.0 g |
| Kalium sorbinicum | 0.14 g |
| Acidum citricum, anhydricum | 0.07 g |
| Aqua purificata | 63.79 g |

TABLE 9

"Cremor nonionicus emulsificans aquosum" containing 1% Neramexane

| Description | Amount |
|---|---|
| Neramexane mesylate | 1.0 g |
| Cremor nonionicus emulsificans aquosum | 99.0 g |

TABLE 10

"Cremor nonionicus emulsificans aquosum"
containing 10% Neramexane

| Description | Amount |
| --- | --- |
| Neramexane mesylate | 10.0 g |
| Cremor nonionicus emulsificans aquosum | 90.0 g |

Formulation Example 4

TABLE 11

"Macrogoli unguentum"

| Description | Amount |
| --- | --- |
| Macrogolum 300 | 50.0 g |
| Macrogolum 1500 | 50.0 g |

TABLE 12

"Macrogoli unguentum" containing 2% Neramexane

| Description | Amount |
| --- | --- |
| Neramexane mesylate | 2.0 g |
| Macrogoli unguentum | 98.0 g |

TABLE 13

"Macrogoli unguentum" containing 15% Neramexane

| Description | Amount |
| --- | --- |
| Neramexane mesylate | 15.0 g |
| Macrogoli unguentum | 85.0 g |

Formulation Example 5

TABLE 14

"Linimentum nonionicum aquosum"

| Description | Amount |
| --- | --- |
| Alcohol cetylicus et stearylicus emulsificans nonionicum | 10.5 g |
| 2-Ethylhexylis lauras | 5.0 g |
| Glycerolum 85% | 2.5 g |
| Kalium sorbinicum | 0.14 g |
| Acidum citricum, anhydricum | 0.07 g |
| Aqua purificata | 81.79 g |

TABLE 15

"Linimentum nonionicum aquosum" containing 3% Neramexane

| Description | Amount |
| --- | --- |
| Neramexane mesylate | 3.0 g |
| Linimentum nonionicum aquosum | 97.0 g |

TABLE 16

"Linimentum nonionicum aquosum" containing 12% Neramexane

| Description | Amount |
| --- | --- |
| Neramexane mesylate | 12.0 g |
| Linimentum nonionicum aquosum | 88.0 g |

TABLE 17

"Linimentum nonionicum aquosum" containing 25% Neramexane

| Description | Amount |
| --- | --- |
| Neramexane mesylate | 25.0 g |
| Linimentum nonionicum aquosum | 75.0 g |

EXAMPLES

The following examples illustrate the invention without limiting its scope.

Example 1

Effects of Neramexane on Acetyl Choline-Induced Mast Cell Activation

Neramexane is tested for its ability to inhibit mast cell degranulation in vitro.

Materials and Methods

Cell Culture

The human mast cell line HMC-1 is obtained from J. H. Butterfield (Minnesota, USA) and cultured under standard conditions in RPMI Medium 1640 (GIBCO, Karlsruhe, Germany) at 37° C. For functional assays, the calcium concentration of the medium is adjusted to 1 mM.

Functional Assays

The Mast cell degranulation is monitored by determination of histamine concentration in the culture medium using a sandwich-ELISA from IBL (Hamburg, Germany).Histamine concentration is determined in untreated cells, medium without cells, HMC-1 cells treated with calcimycin, (a calcium ionophore,used as positive control). Additional controls to check reagibilty of the cells are LPS (lipopolysaccharide) and PMA (phorbol 12-myristate 13-acetate). Histamine concentration is determined 10 minutes after addition of the respective substances. Nicotine and choline are used as stimulus for nAChR, muscarine as stimulus for mAChR, and a combination of acetylcholine and eserine (an acetylcholinesterase inhibitor) is used as pancholinergic stimulus. Neramexane is tested at concentrations ranging from 10E-6M to 10E-16M and is added to the culture medium 5 minutes prior to the respective cholinergic stimulus. All experiments are performed twice in quadruplicate.

Evaluation of Data

Statistical analysis is performed using the Wilcoxon sum-of-ranks test (available on www.statpages.net).

In order to determine the sensitivity of mast cells towards cholinergic signals, the HMC-1 cell line cultured under standard conditions with either low or high calcium concentrations is used. Using low calcium, the HMC-1 cells remain unresponsive to ACH, nicotine and calcimycine. Elevation of the calcium concentration to 1 mM renders the HMC-1 cells highly sensitive towards cholinergic stimulation. ACh, choline and nicotine dose-dependently produce mast cell degranulation evidenced by histamine concentration in the culture supernatant. Nanomolar concentrations of ACh and nicotine are sufficient to induce complete degranulation. The specificity of the obtained effect may be demonstrated by preincubation of the HMC-1 cells with anticholinergic substances. Neramexane-mesylate inhibits the observed effects in equimolar concentrations and, dose-dependently, even in lower concentrations than the respective agonist. No histamine liberation is produced by addition of muscarine to the culture medium. These results are shown in FIG. 1.

Results

Neramexane demonstrates a dose-dependent inhibitory effect on mast cell degranulation. These results indicate that neramexane may be useful in treating mast cell mediated diseases such as urticaria, atopic dermatitis, psoriasis, pruritus, asthma, rhinitis, mastocytosis, conjunctivitis and keratoconjunctivitis.

These results further indicate that neramexane may be useful in treating mast cell mediated diseases such food allergy.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference.

The invention claimed is:

1. A method of treating a mast cell mediated disease selected from pruritus, asthma, rhinitis, mastocytosis, conjunctivitis, keratoconjunctivitis, and food allergies, in a subject in need thereof, comprising administering an effective amount of a 1-amino-alkylcyclohexane derivative selected from neramexane and pharmaceutically acceptable salts thereof.

2. The method according to claim 1, wherein the 1-amino-alkylcyclohexane derivative is neramexane mesylate.

3. The method according to claim 2, wherein neramexane mesylate is administered in a range from about 5 mg to about 150 mg/day.

4. The method according to claim 2, wherein neramexane mesylate is administered in a range from about 5 mg to about 100 mg/day.

5. The method according to claim 2, wherein neramexane mesylate is administered at about 5 mg to about 75 mg/day.

6. The method according to claim 2, wherein neramexane mesylate is administered at about 50 mg/day.

7. The method according to claim 2, wherein neramexane mesylate is administered at about 75 mg/day.

8. The method according to claim 1, wherein the 1-amino-alkylcyclohexane derivative is administered once a day, twice a day (b.i.d.), or three times a day.

9. The method according to claim 1, wherein the 1-amino-alkylcyclohexane derivative is administered in a topical formulation.

10. The method according to claim 9, wherein the 1-amino-alkylcyclohexane derivative is administered between 0.1 and 99% by weight of the formulation.

11. The method according to claim 1, wherein the 1-amino-alkylcyclohexane derivative is administered in an oral formulation.

* * * * *

UNITED STATES PATENT AND TRADEMARK OFFICE
CERTIFICATE OF CORRECTION

| | | |
|---|---|---|
| PATENT NO. | : 8,680,149 B2 | Page 1 of 1 |
| APPLICATION NO. | : 13/766145 | |
| DATED | : March 25, 2014 | |
| INVENTOR(S) | : Hjalmar Kurzen | |

It is certified that error appears in the above-identified patent and that said Letters Patent is hereby corrected as shown below:

Title Page, under References Cited, Col. 2, Foreign Patent Doc: "WO01/88253" should be --WO01/98253--.

Signed and Sealed this
Twentieth Day of May, 2014

Michelle K. Lee
*Deputy Director of the United States Patent and Trademark Office*